(12) United States Patent
Porter et al.

(10) Patent No.: US 7,604,953 B2
(45) Date of Patent: Oct. 20, 2009

(54) BIOAMPLIFICATION FOR MICROBIAL SENSOR SIGNAL TRANSDUCTION

(75) Inventors: Marc D. Porter, Salt Lake City, UT (US); Betsy Jean Yakes, Alexandria, VA (US); Robert J. Lipert, Ames, IA (US); John P. Bannantine, Ames, IA (US)

(73) Assignees: Iowa State University Research Foundation, Inc., Ames, IA (US); The United States of America as represented by the Department of Agriculture/Cooperative State Research Education and Extension Service (USDA/CSREES), Washington, DC (US)

( * ) Notice: Subject to any disclaimer, the term of this patent is extended or adjusted under 35 U.S.C. 154(b) by 0 days.

(21) Appl. No.: 12/130,528

(22) Filed: May 30, 2008

(65) Prior Publication Data

US 2009/0017480 A1 Jan. 15, 2009

Related U.S. Application Data

(60) Provisional application No. 60/949,727, filed on Jul. 13, 2007.

(51) Int. Cl.
*G01N 33/53* (2006.01)
*C12Q 1/00* (2006.01)
*A61K 39/04* (2006.01)

(52) U.S. Cl. .............................. 435/7.1; 435/4; 424/9.1; 424/9.2; 424/130.1; 424/163.1; 424/164.1; 424/178.1; 424/234.1; 424/248.1

(58) Field of Classification Search .................. 424/9.1, 424/9.2, 130.1, 163.1, 164.1, 178.1, 234.1, 424/248.1; 435/4, 7.1
See application file for complete search history.

*Primary Examiner*—Rodney P. Swartz
(74) *Attorney, Agent, or Firm*—McKee, Voorhees & Sease, P.L.C.

(57) ABSTRACT

A process of detection of the causative agent of Johne's disease (*Mycobacterium avium* subsp. *paratuberculosis*) (MAP) by detecting shedding of surface protein of MAP. A preferred way is use of surface enhanced Raman Spectroscopy. The system of detecting MAP shedding of protein provides early detection and diagnosis, and therefore allows early treatment for Johne's disease in ruminant animals.

8 Claims, 6 Drawing Sheets

BIOAMPLIFICATION FOR MICROBIAL SENSOR SIGNAL TRANSDUCTION

CROSS-REFERENCE TO RELATED APPLICATIONS

This application claims priority under 35 U.S.C. § 119 of a provisional application Ser. No. 60/949,727 filed Jul. 13, 2007, which application is hereby incorporated by reference in its entirety.

GRANT REFERENCE

This invention was made with government support under DARPA contract no: MDA972-02-2-0002. The government has certain rights in the invention.

BACKGROUND OF THE INVENTION

Johne's disease has been reported in almost all countries around the world. Johne's disease or *paratuberculosis*, is a chronic wasting disease that causes considerable production losses in adult cattle, sheep, goats, deer, llamas, elk, bison, and other ruminants. The disease is caused by *Mycobacterium paratuberculosis*, a bacterium related to tuberculosis.

Johne's disease typically starts as an infection in calves, though visible signs do not generally appear until cattle are 2 to 5 years of age (and sometimes much older). The infection is difficult to detect in its early stages. This bacterium causes an inflamed intestinal tract, results in severe weight loss, diarrhea and lower milk production. Infected cattle frequently eat well, and look bright, however, they appear to be unthrifty. Body temperature may be or may not be elevated. There is no cure for Johne's disease once an animal becomes infected.

Eradication of Johne's disease is extremely difficult because of its insidious nature, long incubation period, difficulty in early detection, and major management changes necessary to prevent and eradicate it. Consultation and action by a veterinarian experienced in the management of Johne's disease is necessary for the development of heard-control and eradication program.

The causative agent of Johne's disease is *Mycobacterium avium* subsp. *paratuberculosis*, MAP. This infection is found in domestic ruminants (e.g., cattle, sheep and goats and wildlife and is responsible for overwhelming losses in dairy production worldwide. Animals that are afflicted with MAP progress from silent infection to a subclinical phase in which no physical symptoms are present; however, subtle levels of shedding can contaminate the heard during these stages. Once the physical symptoms of weight loss and chronic diarrhea are present at the clinical and advanced cellular disease phases, the damage to the cattle population has already occurred with resulting large financial losses to the farmer and the cattle industry.

Diagnosis of the disease in live individual animals is difficult for a number of reasons. To date, "there is no single, good test for *paratuberculosis*. As a result a combination of tests is often used." It seems that it is easier to diagnosis the presence in a herd as opposed to individual animals. Most of the time, the definitive diagnosis is done after an animal has died. There is current research occurring to attempt to develop better diagnostic methods for this difficult disease.

To control the spread of this disease, a detection method must be rapid, field worthy, cost effective, sensitive to low levels of shedding, and selective for MAP over other commonly occurring bacteria. Currently available methods tend to fall short of these goals as bacteriologic culturing methods are lengthy (12-16 weeks); serological tests suffer from a lack of sensitivity at subclinical levels; and gamma interferon and nucleic acid probe tests have low specificity.

In view of the shortfall of bacteriologic culture methods, serologic tests, interferon and nucleic acid probe tests, there is a continuing need for a simple field worthy test that can be inexpensively run and quickly run to improve upon current techniques for early detection of Johne's disease. This invention has the development of such a test as its primary objective.

BRIEF SUMMARY OF THE INVENTION

A process of detection of the causative agent of Johne's disease (*Mycobacterium avium* subsp. *paratuberculosis*) (MAP) by detecting shedding of surface protein of MAP. A preferred way is use of surface enhanced Raman Spectroscopy (SERS). The system of detecting MAP shedding of protein provides early detection and diagnosis, and therefore allows early treatment for Johne's disease in ruminant animals.

DETAILED DESCRIPTION OF THE PREFERRED EMBODIMENT

Figure 1:
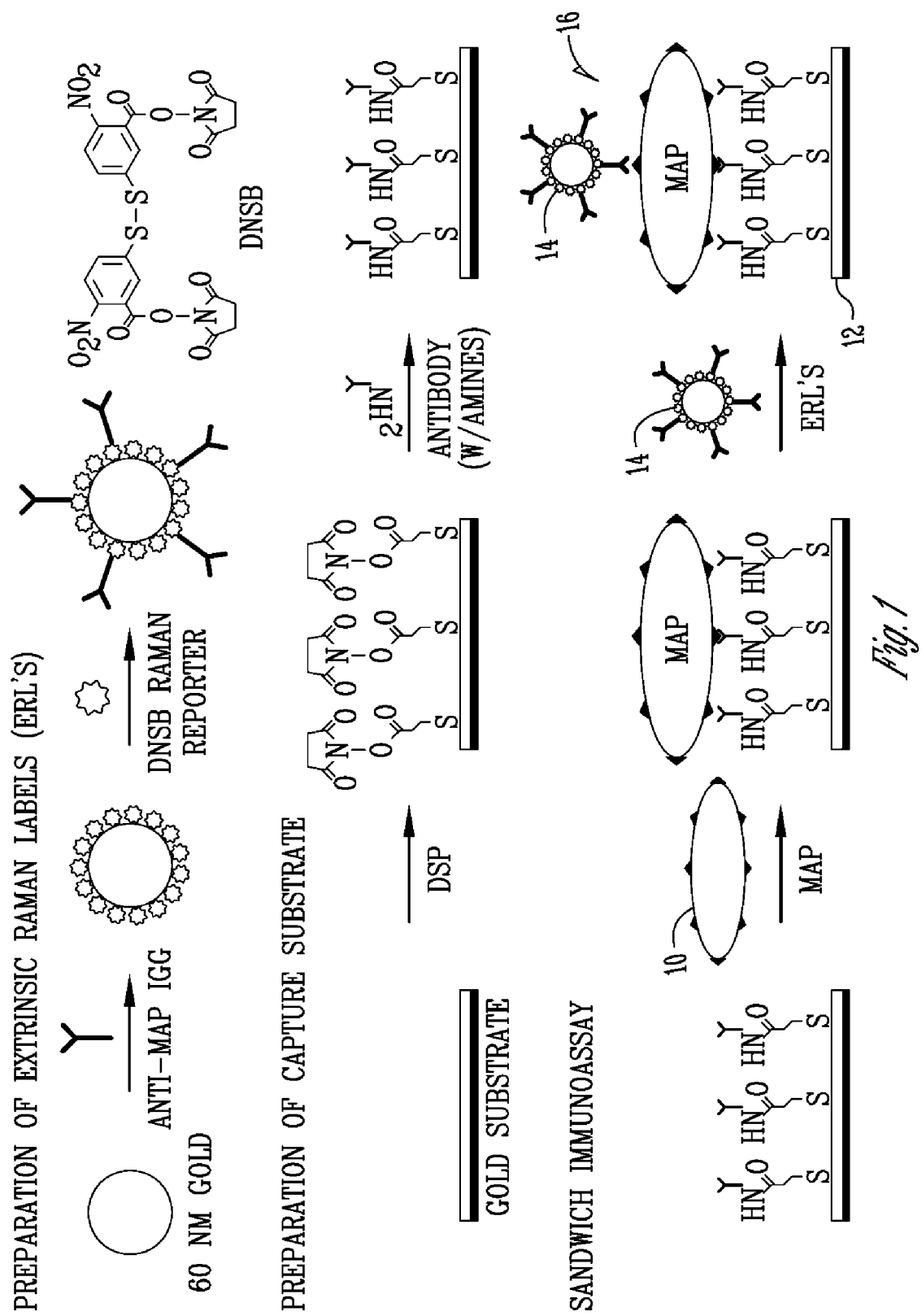
FIG. 1 shows the step-by-step preparation of a novel SERS based sandwich aminoassay.

Earlier inventions of some of the co-inventors relate to specific SERS processes and improvements in preparation of extrinsic Raman labels (ERLS). For the general description of SERS and the preparation of assays for use in the same, Applicants incorporate by reference the pending applications of some of the same inventors here, Porter et al, U.S. patent application Ser. No. 09/961,628 filed Sep. 24, 2001 and Porter et al, U.S. patent applicant Ser. No. 10/931,142 of Aug. 31, 2004, which is a Continuation-in-part of the earlier referenced Porter et al application.

Raman Spectroscopy measures the level of Raman scattering induced by the application of a radiation source, i.e., light source, on an analyte. The light incident on the analyte is scattered due to excitation of electrons in the analyte. "Raman" scattering occurs when the excited electron returns to an energy level other than that from which it came, resulting in a change in the wavelength of the scattered light and giving rise to a series of spectral lines at both higher and lower frequencies than that of the incident light. The series of spectral lines is generally called the Raman spectrum.

Conventional Raman Spectroscopy usually lacks sufficient sensitivity for use as a readout method for immunoassays. However, a modified form of Raman Spectroscopy based on the surface enhanced Raman scattering (SERS) has proved to be more sensitive and thus of more general use in diagnostics. In the SERS form of Raman Spectroscopy the analyte whose spectrum is being recorded is closely associated with a roughened metal surface. This close association leads to a large increase in the detection sensitivity, the affect being greater the closer the proximity of the analyte to the metal surface. The earlier referenced applications of some of the co-inventors described the application of SERS for detection in immunoassays.

As earlier mentioned, the basis of SERS theory lies in the use of roughened metal surface to amplify normal Raman scattering, an inelastic scattering of light due to a vibrational transition and change in polarizability of a molecule, to levels of up to $10^{15}$ times. This enhancement of Raman scattering is due to two effects: chemical and electromagnetic. Chemical enhancement is based on a new charge-transfer state being formed between the metal surface and the absorbed, organic molecule that allows for Raman scattering. While it is believed that chemical enhancement contributes up to 100 times to the overall Raman enhancement seen in SERS, this short range effect only accounts for a minute portion of the total SERS enhancement.

Electromagnetic enhancement can account for the rest of the SERS signal enhancement over traditional Raman spectroscopy. When light is incident on a metal surface, conduction electrons in the metal can collectively oscillate. This processes, known as surface Plasmon resonance, is caused by specific wavelengths which are dependent on the particle/metal asperity size, shape, and the dielectric properties of metal and surrounding medium. Much work has been done to mathematically model this theory and has allowed for better predictability of materials that will lead to enhanced SERS. The most interesting results of these theories indicate that a molecule does not need to be directly on the surface of the metal and that the best laser wavelength for enhancement is one that is between the surface Plasmon frequency of the metal and the scattering frequency of the Raman molecule. Experiments to verify these theories have only recently been performed and the results compare well with expected mathematical trends.

The method developed here, capitalizes on these theoretical considerations by using a novel SERS-based sandwich immunoassay (FIG. 1). In this preferred format for practice of the invention, a biologically active molecule (MAP) 10 is tethered between a metal surface 12 and an extrinsic Raman label (ERL) 14 via specific antibodies 16. When using a gold substrate surface 12 as well as 60-nm colloidal gold functionalized with reporter molecules containing a nitro group, the correct laser excitation wavelength is approximately 632.8 nm (He—Ne laser) for optimal scattering. It has also been shown that when the distance between the ERLs 14 and the gold substrate surface is increased, the SERS signal decreases. With this experimental and theoretical evidence, it is expected that signals from MAP bacteria 10 with a height of ~0.5 μm will yield much smaller SERS signals than the small (35-KDa) protein captured from the protein lysate based purely on SERS distance dependence. This invention demonstrates the assay performance using MAP bacteria and proves low detection limits (~500 cell/mL) can be achieved to allow early Johne's disease detection. This in turn can allow early isolation and treatment.

What has been discovered and not previously known is that dead MAP present in, for example, milk of an infected cow, shed a protein covering that can be detected easily to establish an early diagnosis and allow treatment soon, before substantial herd infection. The shed protein amplifies the bacteria signal. This has not heretofore been recognized nor taken advantage of to allow early detection and diagnosis.

The following examples are shown to demonstrate the materials used, the methods employed, and the results achieved and to demonstrate efficacy of the assay. It goes without saying that certain modifications can be made and still achieve the benefits of the invention. Such modifications and their equivalence are intended to be within the scope of the written description, the disclosed best mode and the claims.

While the following examples describe SERS as the heterogeneous immunoassay, others can be used such as scintillation counting, fluorescence, chemiluminescence, electrochemical assays and enzymatic methods, surface plasmon resonance, quantum dots, and microcantilevers.

EXAMPLES

MAP, K-10 strain bacteria were cultured at the National Animal Disease Center (NADC, Ames, Iowa) as described previously (Yakes, et al. "*Detection of Microbacterium avium subsp. paratuberculosis using Surface-Enhanced Raman Scattering: Part I-Sonicate Immunoassay Development, in preparation*") by culturing in Middlebrook's 7H9 medium (Becton Dickinson, Cockeysville, Md.) supplemented with mycobactin J (Allied Monitor Inc., Fayette, Mo.), oleic acid albumin-dextrose complex (Difco, Detroit, Mich.), and Tween 80 (Sigma Chemical Co., St. Louis, Mo.). The bacilli were removed by centrifugation, washed with cold phosphate buffered saline solution (PBS; 0.15 M, pH 7.2), and heat treated at 80° C. for 30 min. All heat-killed, whole cell bacterial concentrations were determined by flow cytometry using LIVE/DEAD® BacLight™ Bacterial Viability and Counting Kit (Molecular Probes, Eugene, Oreg.). The average value was $1.3 \pm 0.3 \times 10^7$ bacteria/mL over six aliquots from a stock of MAP in PBS. These values were further confirmed by culturing and enumeration via serial dilution planting on Herrold's egg yolk slants containing mycobactin J (2 mg/liter).

Antigen solutions were prepared by serial dilution of the $1.3 \times 10^7$ MAP/mL stock solution with 10 mM PBS (pH 7.4, 10 mM powder packs, Sigma-Aldrich). Between each dilution, solutions were briefly vortexed to ensure homogeneity of the sample concentration. Distilled water, subsequently deionized with a Millipore Milli-Q system (18 MΩ), was used for preparation of all aqueous reagents. Pasteurized, whole milk at room temperature was used for serial dilutions in place of the 10 mM PBS for the assays employing a whole milk sample matrix.

The monoclonal antibody (mAb), termed 13E1, is specific to MAP2121c, a MAP membrane protein. The MAP2121c protein was recombinantly produced in *E. coli*(2) and then subsequently used to immunize mice for production of mAbs (3).

13E1 mAb was purified from tissue culture supernatants using Melon Gel (Pierce, Rockford, Ill.). Concentration of the antibody solution was determined by ND-1000 Spectrophometer (NanoDrop, Wilmington, Del.) measurements. All dilutions of 13E1 mAb were achieved with 50 mM borate buffer (pH 8.3 borate buffer packs, Pierce).

In the previous applications incorporated by reference, a detailed procedure for formation of selective ERLs is outlined. Briefly, 1.0 mL of 60 nm gold particles (<8% variation in diameter, $2.6 \times 10^{10}$ particles/mL, Ted Pella, Redding, Calif.) was buffered with 40 μL of 50 mM borate buffer (pH 8.3) and 10 μL of 1 mM 5,5'-dithiobis (succinimidyl-2-nitrobenzoate), DSNB, in acetonitrile were added. The DSNB Raman scatterer chemisorbs to the nanoparticles through formation of sulfur to gold bonds and serves as the Raman scatter. After 7 h of incubation, 20 μg of 13E1 mAb were added and allowed to react overnight thus enabling an amide linkage of the amines on the mAb to the succinimidyl esters of the DSNB-derived monolayer. Finally, 100 μL of 10% bovine serum albumin (BSA, Sigma-Aldrich) in 2 mM borate buffer were added to the suspension and reacted for 7 h in order to block any unreacted succinimidyl esters.

For removal of any excess reagents, the colloidal suspension was then centrifuged (Eppendorf MiniSpin, Westbury, N.Y.) at 2000 g for 10 min. The supernatant solution was removed, and the loose ERL pellet was resuspended in 1000 μL of 2 mM borate buffer containing 1% BSA. This process was repeated twice to ensure removal of unreacted materials, and the final resuspension of the ERLs was in 500 μL, half of the original volume in order to concentrate the nanoparticle solution. In addition, 50 μL of 10% sodium chloride (NaCl, Sigma-Adlrich) was added to the reacted nanoparticles to mimic biological conditions. Finally, in order to remove any aggregates, the particles were filtered through a 0.22-μm syringe filter (Costar, Fisher).

The capture surface was prepared as follows. Gold substrates were prepared by resistive evaporation of ~300 nm of 99.9% pure gold at a rate of 0.1 to 0.2 nm/s onto a 4-in. ptype, test grade silicon [111] wafer (University Wafer, South Boston, Mass.) using an Edwards 306A evaporator. Cleaned 1×1 cm² glass chips are then applied to the gold surface via a two-part epoxy (Epo-tek 377 part A and B, Billerica, Mass.) and cured at 50° C. for 1.75 h. Template stripped gold (TSG) slides are then separated from the wafer. An octadecanethiol (ODT, Sigma-Aldrich) coated, poly(dimethyl siloxane) (PDMS, Dow Corning, Midland, Mich.) stamp with a 3.2-mm diameter centered hole was used to stamp the smooth gold surface in order to form a hydrophobic barrier surrounding the assay area. TSG was then exposed to 1 mM dithiobis (succinimidyl propionate) (DSP, Sigma-Aldrich) in ethanol (Aaper, Shelbyville, Ky.) for 14 hours in order to form the substrate platform. After rinsing the substrates with ethanol and drying under a stream of nitrogen, 20 μL of 13E1 capture antibody (100 pg/mL) was placed on the substrate for 7 h to allow for the succinimidyl group on the DSP-based monolayer to react with primary amines on the antibody thus forming amide linkages. The substrate was then rinsed three times with 2 mL of 10 mM PBS buffer. Unreacted succinimidyl endgroups of the monolayer were then capped with Super-Block (20 μL drop, Pierce).

After capture surface preparation, the substrate was exposed to varying concentrations of heat-killed, whole cell MAP in 110 mM PBS buffer (pH 7.4) or pasteurized, whole milk. After reacting for 7 h at room temperature in a humidity chamber, the substrates were washed three times with 2 mM borate buffer (pH 8.3) with 150 mM NaCl. Next, a 20 μL drop of ERLs was added. Finally, the assay surfaces were rinsed with 2 mM borate with 150 mM NaCl and gently dried with nitrogen.

SERS spectra for the immunoassay were collected using a NanoRaman™ I spectrometer (Concurrent Analytical, Waimanalo, Hi.) with a He—Ne laser (632.8 nm, 30 mW, 250-μm diameter spot size), fiber-optic-based probe head, an f/2.0 Czerny-Turner imaging spectrometer (6-8 cm⁻¹ resolution), and a 0° C. thermoelectrically cooled CCD (Kodak 040 1 E). Normal incidence laser light was focused onto the substrate surface via a 0.68 numerical aperture objective, and exposure times of either 1 or 5-s were employed and are appropriately specified. The same objective and fiber optic probe also collected the scattered radiation. Spectral data were evaluated using TRCommander 1.3.0 software.

An in-house Raman spectroscopy microscope was used for the protein shedding and single bacterium studies outlined in the results section. This system is composed of an optical microscope (Olympus BH-2, Centervalley, Pa.) and spectrograph (Spectrapro, 300i, Acton Research, Acton, Mass.) with a thinned, back-illuminated, liquid nitrogen-cooled CCD (LN/CCD-1100PB, Princeton Instruments, Trenton, N.J.). For spectral measurements, a 60-mW He—Ne laser (632.8 nm) was attenuated through a variable, neutral density filter (Thorlabs, Newton, N.J.). The light was then focused through a 100× objective onto the substrate that was mounted on the microscope sample stage. The laser light forms an ~1.5 micrometer diameter laser spot size with an incident power of ~1 mW. The scattered light was then collected through the same objective and directed by optics to the spectrograph. All the microscopy-based spectra for the protein shedding and single bacterium studies were collected with a 2-s integration time. Spectral data were evaluated using WinSpec/32 (Princeton Instruments), and microscope images were obtained with ATI Multimedia video software (ATI Technologies, Markham, Ontario).

SEM images were obtained using a JEOL 59101v instrument (Tokyo, Japan). Each sample was sputter coated with a thin layer of gold prior to loading in the SEM chamber. For each SEM image, a working distance of 10 mm and an accelerating voltage of 15 kV were used. All images reported herein are from secondary electrons.

Figure 2:
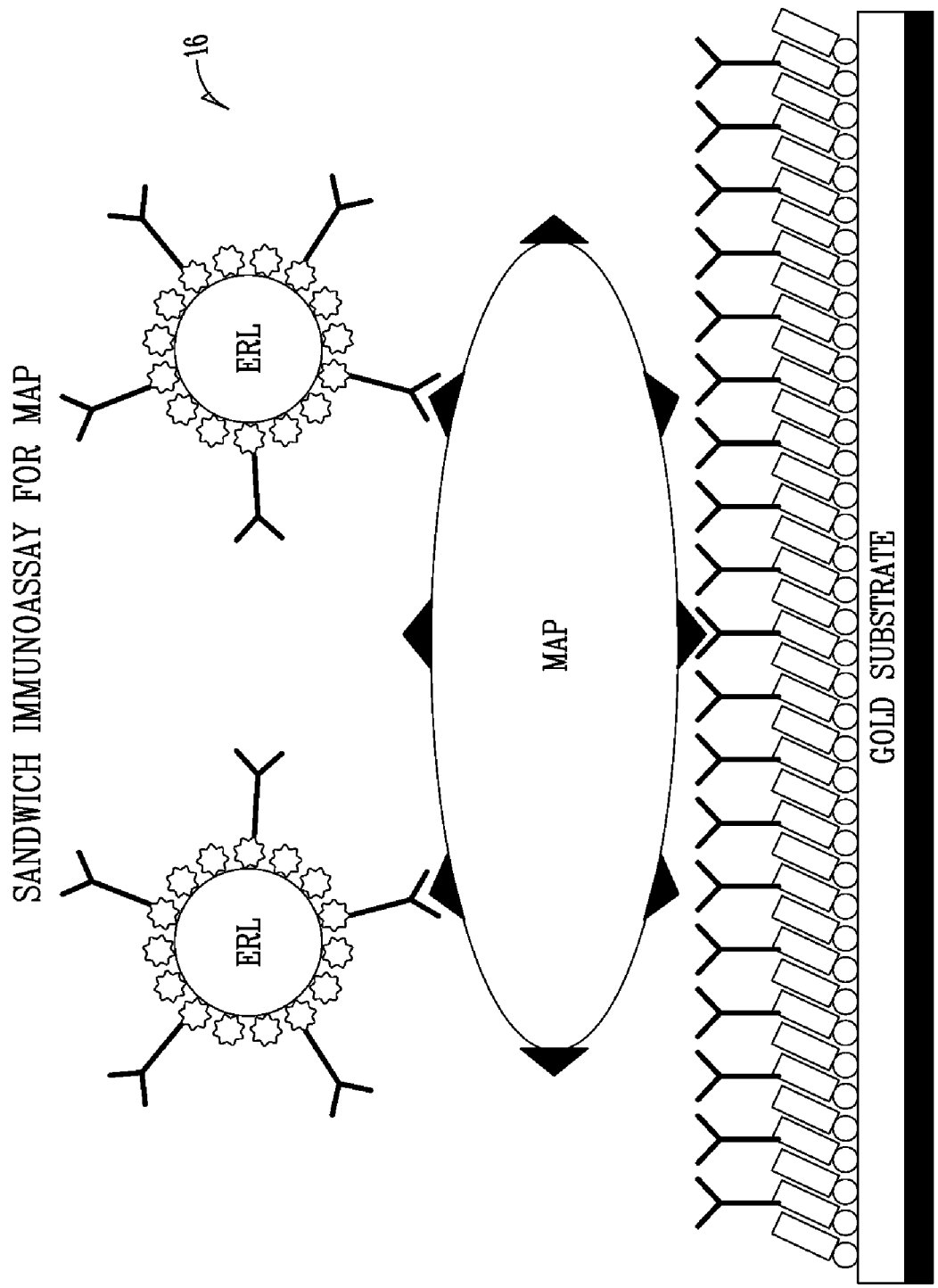
FIG. 2 shows the sandwich immunoassay for MAP, attached to a gold substrate.
Figure 3:
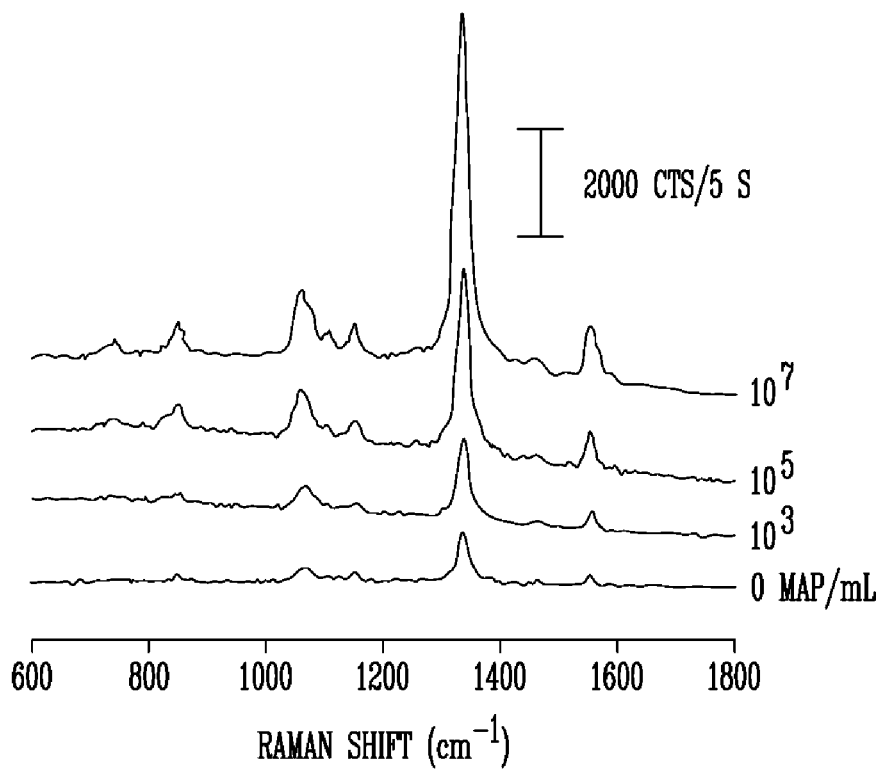
FIG. 3 shows a SERS Spectra calibration curve.

After forming the assay platform by immobilizing the 13E1 mAb on the DSP-derived monolayer, heat-killed, whole cell MAP with concentrations ranging from 0 to $1.0\times10^7$ MAP/mL in PBS were incubated with the capture surface platform as shown schematically in FIGS. 1 and 2. Following rinsing, the substrate surfaces were exposed to the ERLs as shown in FIG. 1c. After another rinsing step and drying, each platform was read out with an integration time of 5-s, yielding the SERS spectra and calibration curve shown in FIG. 3. Spectral features that are consistent with a DSNB-derived monolayer are seen in FIG. 3 with the strongest peak in the spectrum at 1336 cm⁻¹ attributed to the symmetric nitro stretch, $v_s(NO_2)$. The less intense peaks at 1062 cm⁻¹ and 1554 cm⁻¹ most likely arise from aromatic ring modes. As the concentration of bacteria in the antigen solutions increased, it was expected that the number of ERLs bound to the assay surface and thus the SERS signal would also increase. Indeed, the spectral peaks did increase in height as the concentration of MAP increases.

To create a standard calibration curve for the spectral data in FIG. 3, the SERS intensity was calculated by subtracting the background at 1225 cm⁻¹ from the peak signal at 1336 cm⁻¹. These signals for each individual solution concentration (average of five measurements at different locations on a single slide) were then plotted versus the concentration of bacteria in the antigen solution. As discussed above, the expected trend of an increase in SERS intensity with an increase in MAP concentration, is easily seen in FIG. 4. The lowest detectable signal is defined as the blank signal plus three times the standard deviation of the blank and is shown as the dashed line in the calibration curve. Where the calibration curve intersects this line is defined as the limit of detection (LOD), which in this assay is $6.3\times10^2$ MAP/mL.

Figure 5:
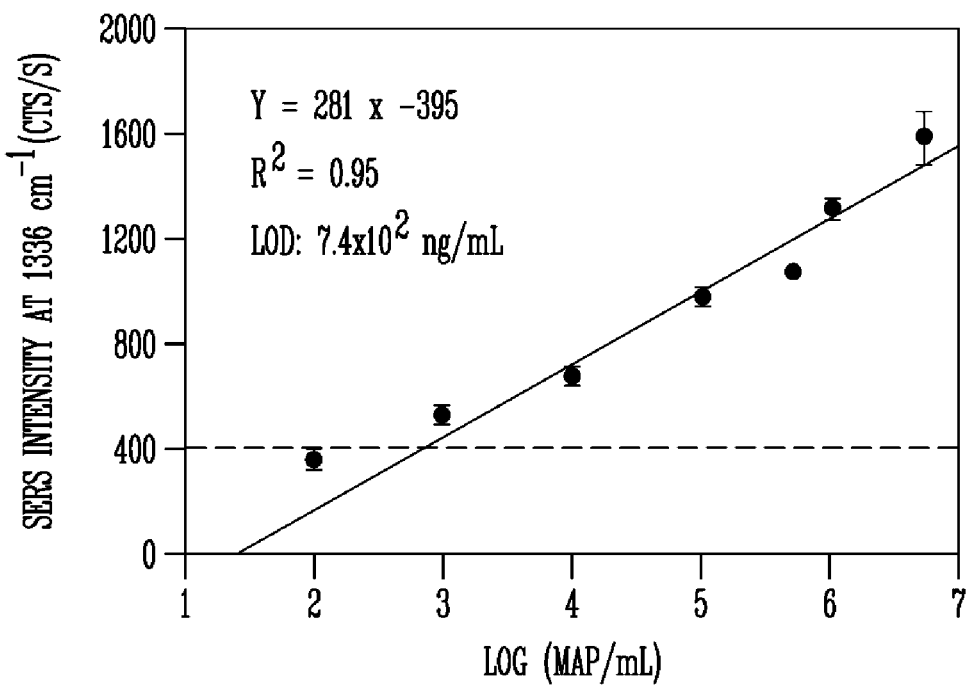
FIG. 5 shows a calibration curve of heat-killed, whole cell MAP in a milk matrix.

To further extend the assay to the analysis of relevant and complex samples, studies were carried out using pasteurized, whole milk for a sample matrix. Room temperature milk was spiked with heat killed, whole cell MAP with final concentrations ranging from 0 to $5.0\times10^6$ MAP/mL. After performing the assay procedure discussed above, the calibration curve in FIG. 5 was obtained. Using the same LOD determination, the simulated, real world matrix study has a LOD of $7.4\times10^2$ MAP/mL. The calibration curve for PBS (FIG. 3) and milk matrices (FIG. 5) as well as the LOD for each experiment are quite similar (within a factor or two for LOD).

For immunoassays, the logistic model indicates that there should be linearity over approximately three orders for a two-site (sandwich) immunoassay. However, as previously noted, there are five orders of linearity for the MAP assay. In addition, the theoretical LOD for the SERS-based immunoassay is on the order of $8\times10^5$ cells/mL; however, the LOD that was experimentally determined was ~500 MAP/mL. These discrepancies in theory versus experimental results led to investigations to evaluate the signal amplification per bacterium which may account for the lower LOD. To determine if protein was being shed from the bacteria and then binding to the assay surface thus creating signal amplification, two experiments were performed. Both experiments were designed to determine if free protein was present in the bacterial solution and, if so, was binding to the assay substrate. These assays were performed in parallel, using MAP concentrations ranging from 0 to $1.3\times10^7$ MAP/mL in PBS. After adding antigen to the first set of capture substrates, the vials containing the bacteria were spun down in a centrifuge at 7,000 rpm for 10 min to pellet out the bacteria, and 20 μL of the resulting supernatant was pipetted onto the second set of capture substrates.

After completing the incubation steps of antigenic solution and then ERLs, the SERS signals and light microscope images of each sample were obtained. Microscope images (data not shown) revealed that: (1) bacteria had bound to the substrates exposed to the whole cell bacteria solution and (2) no bacteria were detectably captured on the slides treated to only the supernatant solution indicating that the centrifugation did remove bacteria from the solution.

Figure 6:
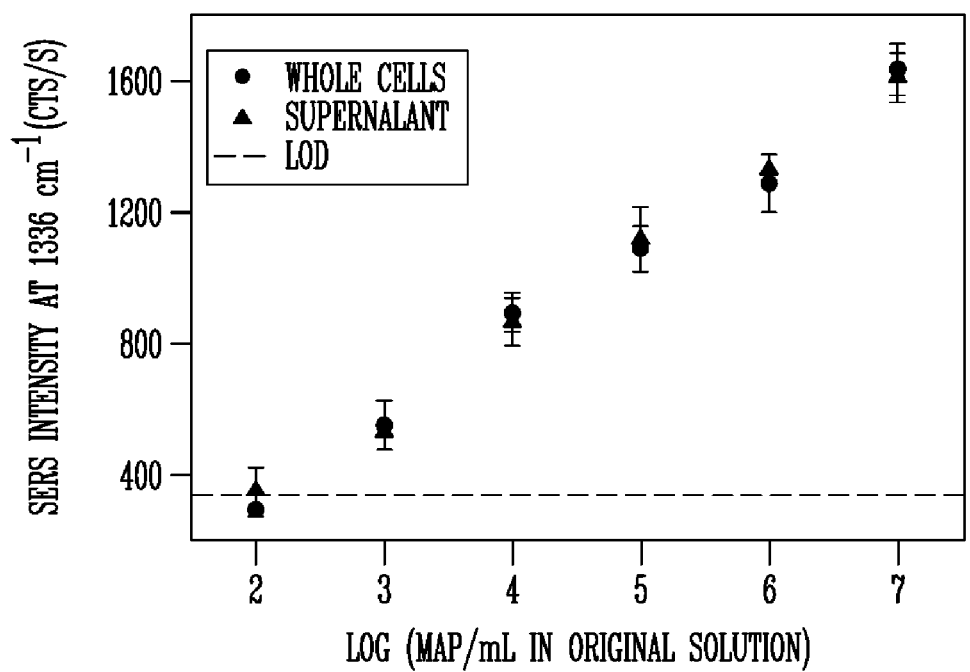
FIG. 6 shows the plots obtained from the assays of the whole MAP and the supernatant of each sample after the bacteria have been removed by centrification.

FIG. 6 shows the plots obtained from the assays of the whole cell MAP and the supernatant of each sample after the bacteria had been removed by centrifugation. The SERS intensity of the peak at 1336 cm$^{-1}$ for the assays is plotted versus the concentration of bacteria that were in the original whole cell MAP solutions. Both plots exhibit an increase in signal with an increase in the original MAP concentration. These results suggest that at least some of the MAP2121c protein is secreted or "shed" in the whole cell solutions and that this "free" protein can bind the ERLs. More importantly, the results suggest that the shed protein adds to the signal for the whole cell assay and is the biggest contributor to the observed response in FIG. 6 as the two curves are virtually superimposed.

Figure 7:
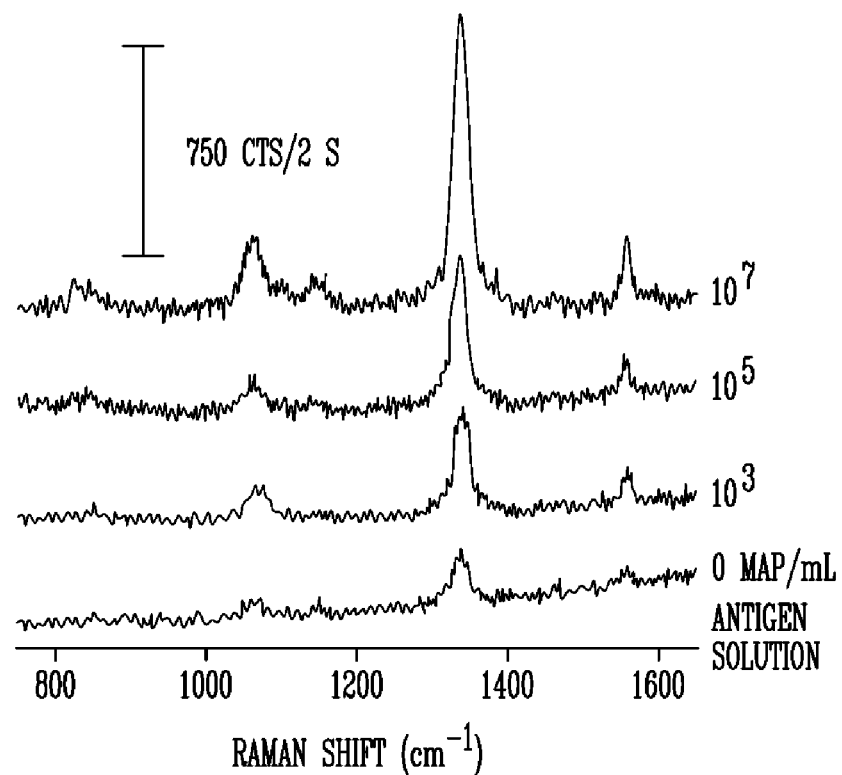
FIG. 7 shows characteristic special features of DSNB-based label.
Figure 8:
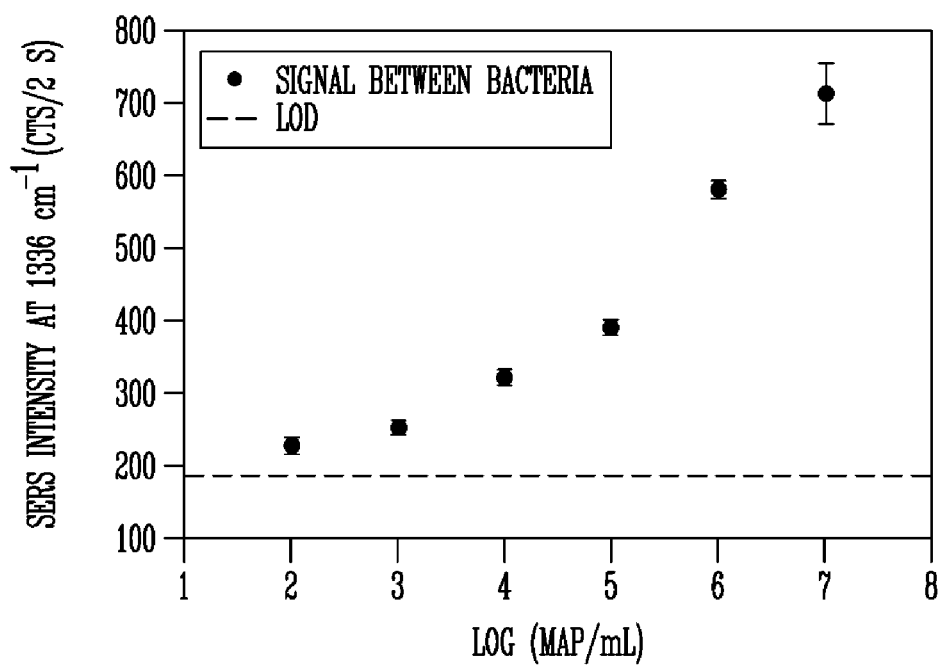
FIG. 8 shows the SERS signals from areas between bacteria increasing as the amount of bacterial and antigen solution increases.

The second experiment was aimed at further testing protein shedding by using an in-house designed Raman Microscope and the capture substrates exposed to whole cell MAP. The optics in this instrument allow the laser spot to focus on either a single captured bacterium or on an area of the assay surface that is devoid of bacteria. When the laser was focused on an area of the slide between bacteria, the SERS spectra and calibration curve in FIGS. 7 and 8 were obtained. The spectra in FIG. 7 have the characteristic spectral features of the DSNB-based label. As shown in FIG. 8, the SERS signals from areas in between bacteria increase as the amount of bacteria in the antigen solution was increased. These data confirm that there is shed protein present on the capture surface an that the amount of free protein in solution increases with an increase in the number of bacteria in that solution.

Figure 4:
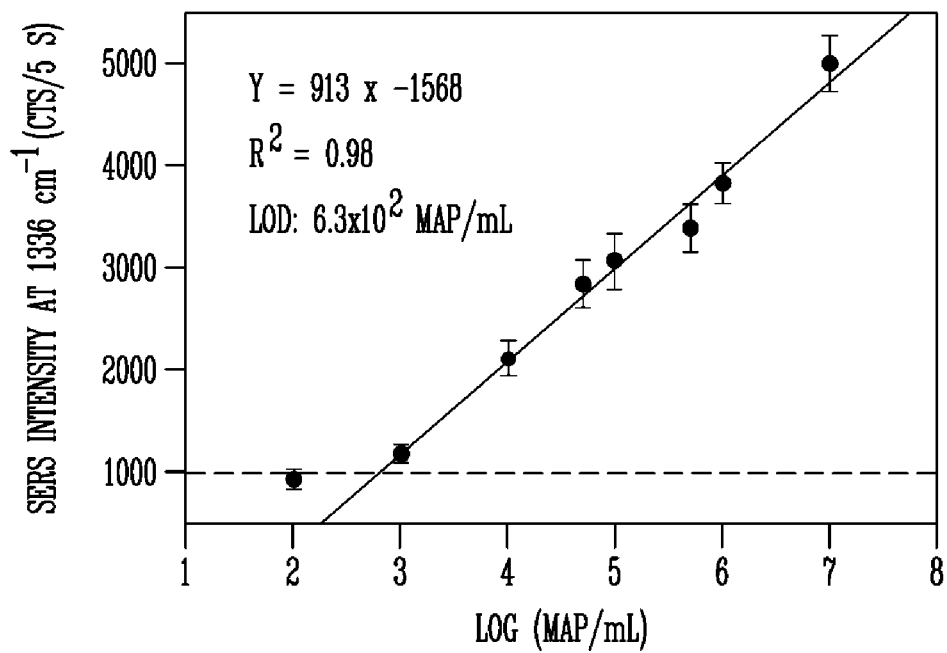
FIG. 4 is a graph and shows SERS intensity with an increase in MAP concentration.
Figure 9:
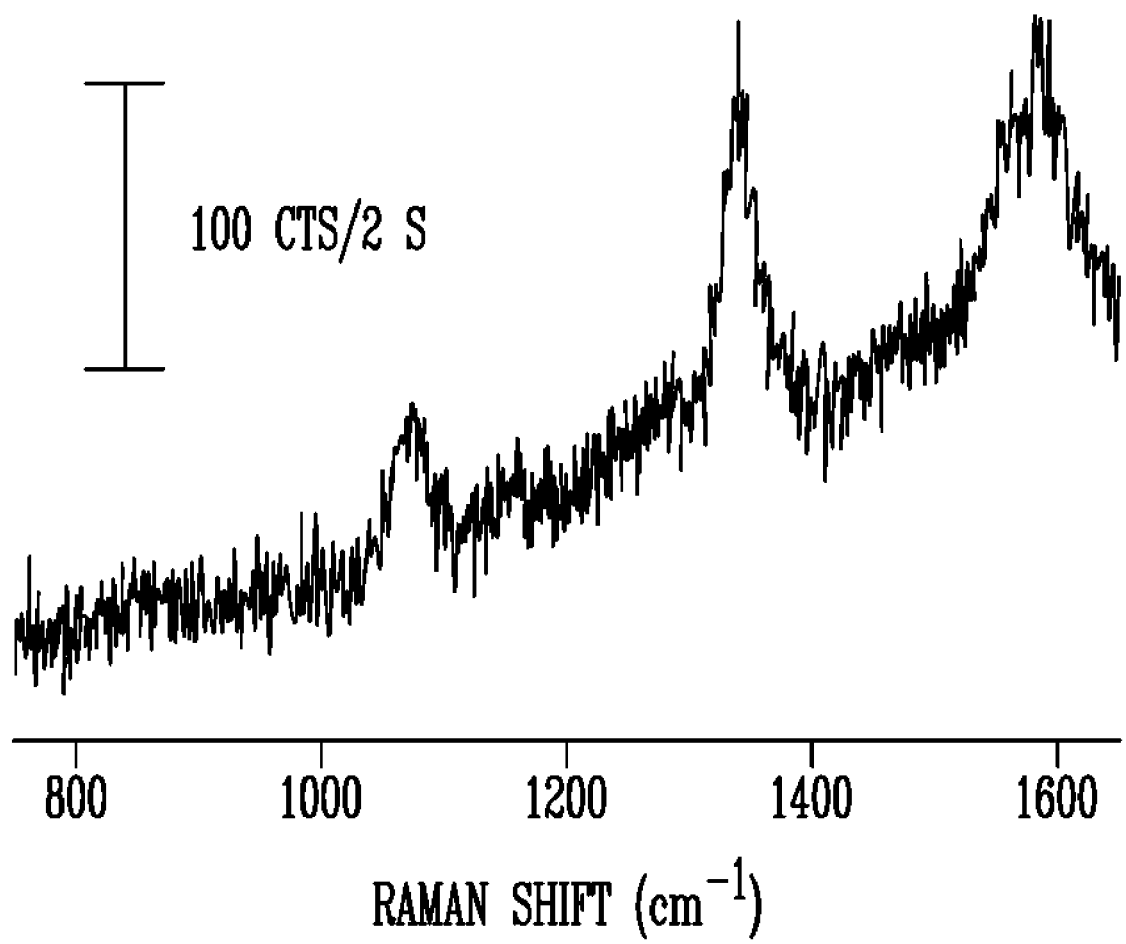
FIG. 9 shows a spectrum where the laser was focused on a single bacterium.

When the laser was focused on a single bacterium, as shown in FIG. 4, a distinct spectrum (FIG. 9) was obtained. While this spectrum has the characteristic peaks of the DSNB reporter molecule, it also has an arching background and broad peak at 1600 cm$^{-1}$, which can be attributed to the underlying bacteria. Upon measuring 11 single bacteria from slides with different original concentrations of antigen solutions, the average SERS intensity from the nitro stretch at 1336 cm$^{-1}$ was 170±11 cts/2 sec. These results indicate that there is SERS signal from the bacteria; however, the SERS signal could arise from ERLs located on the surface surrounding the bacterium or on the bacterium itself.

To determine the location of the ERLs, samples were exposed to a brief water rinse to remove salt residue, dried, sputter coated with gold, and imaged with SEM. Shown in FIG. 7 are two SEM images of a substrate which contained a MAP concentration of $1.3\times10^7$ MAP/mL. A single bacterium is evident in the center of both images which is identified by a rod-like shape and a length and width of approximately 1 μm×0.5 μm. In addition there are several smaller, circular objects that have a size consistent with 60-nm gold particles of the ERLs. Also, many of the nanoparticles are located in areas devoid of bacteria, and there are only a few nanoparticles located on the bacterium. Furthermore, ×10,000 SEM images from blank slides (0 MAP/mL) had very few nanoparticles nonspecifically bound and no bacteria (data not shown). These findings further support the likelihood that shed protein is captured by the assay substrate and that the majority of the response for the whole cell MAP assay arises from ERLs bound to these shed proteins and not the captured bacteria.

In order to improve upon currently available diagnostic tests for Johne's disease, a sandwich immunoassay with SERS readout was made. This method was developed by selecting a nAb (13E1) that has only recently been developed and characterized. After screening for the best blocking agent, experiments were performed in both PBS and milk matrices which yielded levels of detection on the order of 150 ng/mL (750 MAP/mL in the original solution). The SERS-based immunoassay improved upon other detection methods (culturing, serological tests, and tests for cellular immunity) by combining the desirable attributes of a simple, rapid, highly sensitive method for the K10 MAP sonicate that did not suffer from antigenic cross-reactivity.

Theory and previous experimental results have shown that when the distance between the gold nanoparticle containing the Raman labels and the substrate platform are increased, the SERS signal decreases. Due to this observation, the sonicate would then yield more intense SERS signals as the protein from the MAP surface is much smaller than the bacteria itself causing the ERLs to be much closer to the gold substrate. Based on this evidence, optimization of the sandwich immunoassay was performed with MAP sonicate solutions first for ease of use.

Using this sandwich immunoassay, the method was extended to heat-killed, whole cell MAP. MAP spiked samples in PBS yielded an LOD of $6.3\times10^2$ MAP/mL. This level of detection and the linearity of the calibration curve validate that this method can be transferred to the detection and quantitation of the whole bacterium. In addition, upon performing the assay in the more complex milk sample matrix, the level of detection ($7.4\times10^2$ MAP/mL) and calibration curve were nearly identical to those in PBS. This finding elucidates the ability of this assay to be transferred to a real-time, field worthy diagnostic method in which minimal sample workup would be required prior to sample analysis.

Culturing of MAP from contaminated milk is complicated and very few studies have focused of detecting MAP in milk. The test here described is a first step towards creating a platform for rapid, sensitive, and selective immunoassay to address the need for evaluating MAP levels in milk. Research into further improving the assay for milk matricies as well as extending this assay for quantitation of MAP in fecal samples is currently in progress.

This unexpected trend, based on the theory discussed above, led to questions of how the detection scheme was functioning with the whole bacteria. In addition, the theoretical detection limit for this SERS-based sandwich immunoassay can be calculated by assuming that the lowest level of detection is a single bacterium focused in the laser spot. Since the assay surface is a 3.2-mm diameter circle, and the laser spot size is 25 µm, the area of the laser spot size is $4.9 \times 10^2$ µm$^2$, and the assay area is $8.0 \times 10^6$ µm$^2$. Then, assuming one cell in the laser spot size, the number of cells in the assay area is $1.6 \times 10^4$ cells. This number of cells contained on the original 20 µL drop and is then $8.2 \times 10^5$ cells/mL, the theoretical detection limit. As outlined above, the experimental detection limit is much lower, on the order of $5.0 \times 10^2$ MAP/mL. In addition, the linear dynamic range is five orders of magnitude versus the three expected from theoretical models. Clearly, there is a discrepancy between the theoretical and experimental results. The explanation is set forth below.

The 13E1 mAb binds to the major membrane protein on the MAP cell. If this protein (encoded by MAP2121c) is shed either by the cell itself or as induced by sample preparation, the protein could bind to the assay surface followed by binding of the ERL to the protein. Other *Mycobacteria*, specifically *M. bovis* BCG, are known to release cell wall lipids. While the MAP2121c has no signal sequence to suggest it is secreted, recent studies have shown that surface proteins can be readily removed from MAP by brief agitation treatments such as sonication or vortexing and it is possible, that processes used for this assay do exactly that. This shedding would lead to an effective amplification of the signal from an individual cell and thus allow the current detection limit of $5.0 \times 10^2$ MAP/mL to be reasonable. Applicants do not wish to be bound by this theory but believe it to be a logical explanation for the results.

Importantly, this shedding process is passive and not an active secretion process as the mycobacteria are heat treated prior to use. We believe the observed shedding to be caused by sample preparation in which the surface protein is stripped from the bacteria through agitation during the heat killing or antigen solution preparation processes. Furthermore, it is likely that other MAP proteins are stripped off the surface, but that we are only detecting a portion of the proteins as 131E1 only reacts with the MMP. With this in mind, further signal amplification could be obtained by concurrently detecting multiple proteins. To this end, work to further evaluate the shedding process and multiple protein detection are currently under way.

In summary, results of the protein shedding studies suggested three important conclusions: (1) there is shed protein on the assay surface, (2) the amount of protein increases as the original amount of bacteria in the solution was increased, and (3) the bound protein can bind an ERL. These observations account for the discrepancies between the theoretical detection limit and the experimentally obtained LOD when viewing protein shedding as an internal enhancement mechanism for each individual bacterium. Also, through further investigation of this mechanism, as well as other MAP specific antibodies, additional enhancement may be obtained that further improves the LOD.

This method enables quantitative, low levels of detection for the heat-killed, whole cell MAP. This assay is readily adaptable to a diagnostic laboratory setting and possibility as an in-field analysis system based on results in more complex matrices. With the specificity of the newly developed 13E1 mAb, low levels of detection can be achieved with no cross-reactivity to other bacteria that may be in the milk or feces samples.

In conclusion, in the heat-killed, whole cell MAP assay, a surface protein is shed from the bacteria and enhanced SERS signals are obtained due to ERLs binding to the shed protein that is captured on the assay surface. Due in part to this amplification, this novel, SERS-based sandwich immunoassay system allows for a rapid, selective, and low limits of detection test that can translate to complex sample matrices and thus improves upon many of the available diagnostic tests for Johne's disease. This diagnostic test for MAP has the potential to minimize the spread of Johne's disease through more rapid and sensitive detection of MAP and the subsequent separation of infected animals from the herd. In addition, the quantitative nature of this assay could allow for more analytical definitions for characterization of disease stages as well as better analysis of MAP shedding rates and numbers during disease progression.

What is claimed is:

1. A process of detection of *Mycobacterium avium* subsp. *paratuberculosis* (MAP) to diagnose Johne's disease in ruminants, comprising:
    collecting a bacteria sample from the ruminant to be tested;
    heat treating the bacteria sample to allow any MAP present to shed protein from their surface;
    binding the shed protein to a monoclonal antibody specific for MAP or MAP surface protein to provide bound particles to allow detection of the MAP protein; and
    detecting the presence of MAP or MAP shed protein by immunoassaying the bound particles.

2. The process of claim 1 wherein detecting the presence of MAP is by heterogeneous immunoassay system selected from the group consisting of scintillation counting, fluorescence, chemiluminescence, electrochemical assays and enzymatic methods, surface plasmon resonance, surface-enhanced Raman scattering, quantum dots, and microcantilevers.

3. The process of claim 1 wherein detecting the presence of MAP is by attaching said monoclonal antibody to a MAP antigen attached to a substrate and using surface enhanced Raman spectroscopy (SERS) to detect shedding of surface protein of MAP.

4. The process of claim 3 which uses a sandwich immunoabsorbent assay of immunogold nanoparticles and monoclonal antibodies that are specific for MAP surface protein.

5. The process of claim 4 wherein the lower detection limit of shed protein is when there is at least 600 MAP bacteria per mL.

6. The process of claim 4 wherein the lower detection limit of shed protein is when there is at least 500 MAP bacteria per mL.

7. A heterogeneous sandwich immunoassay for use in SERS detection of MAP, comprising:
    an immunogold substrate;
    a MAP antigen attached to said substrate;
    an Extrinsic RL attached to said MAP antigen.

8. A kit for detection of Johne's disease, comprising:
    a Raman active reporter molecule;
    a substrate for a MAP antigen to attach;
    a surface enhancing particle reagent; and
    instructions of using the kit in SERS detection of surface shedding protein of MAP.

* * * * *